US011980910B2

(12) United States Patent
Perez et al.

(10) Patent No.: US 11,980,910 B2
(45) Date of Patent: May 14, 2024

(54) DEVICE FOR DISPERSING IN THE AIR A VAPOR OF A LIQUID SUBSTANCE

(71) Applicant: CAELIMP, Labege (FR)

(72) Inventors: Yoann Perez, Sarrancolin (FR);
Philippe Riviere, Toulouse (FR);
Philippe Pichon, Villeneuve-de-Riviere (FR)

(73) Assignee: CAELIMP, Labege (FR)

( * ) Notice: Subject to any disclaimer, the term of this patent is extended or adjusted under 35 U.S.C. 154(b) by 673 days.

(21) Appl. No.: 17/252,904

(22) PCT Filed: Jun. 18, 2019

(86) PCT No.: PCT/FR2019/051490
§ 371 (c)(1),
(2) Date: Dec. 16, 2020

(87) PCT Pub. No.: WO2019/243734
PCT Pub. Date: Dec. 26, 2019

(65) Prior Publication Data
US 2021/0276028 A1 Sep. 9, 2021

(30) Foreign Application Priority Data

Jun. 18, 2018 (FR) ...................................... 1855310
Nov. 2, 2018 (FR) ...................................... 1860145

(51) Int. Cl.
*B05B 7/16* (2006.01)
*A01M 1/02* (2006.01)
(Continued)

(52) U.S. Cl.
CPC ............. *B05B 7/1613* (2013.01); *A01M 1/02* (2013.01); *A01M 1/2077* (2013.01);
(Continued)

(58) Field of Classification Search
CPC .......... B05B 7/1613; B05B 7/22; A01M 1/02; A01M 1/2077; A01M 7/0003;
(Continued)

(56) References Cited

U.S. PATENT DOCUMENTS 2,140,516 A 12/1938 Cowan
2,651,178 A * 9/1953 Deni ......................... F23R 3/20
239/77

(Continued)

FOREIGN PATENT DOCUMENTS

CN 1777478 A 5/2006
CN 101495813 A 7/2009
(Continued)

OTHER PUBLICATIONS

International Search Report for corresponding PCT application No. PCT/FR2019/051490, dated Nov. 22, 2019.
(Continued)

*Primary Examiner* — Steven J Ganey
(74) *Attorney, Agent, or Firm* — Notaro, Michalos & Zaccaria P.C.

(57) ABSTRACT

A device for dispersing in the air in the vapor state and a substance that is in the liquid state at ambient temperature, and is contained in a storage container, has a ventilation system with a duct that opens out into the open air and is configured to permit the passage of a flow of air into the duct; at least one dispensing unit is designed to be supplied with a liquid substance by the storage container, the dispensing unit having micro-ducts forming an outlet is provided in the duct in order to constitute an area of evaporation of the substance therein, and a heating unit is provided on or in the dispensing unit, such as to control a flow of the substance through the dispensing unit.

60 Claims, 9 Drawing Sheets

(51) Int. Cl.
  *A01M 1/20* (2006.01)
  *A01M 7/00* (2006.01)
  *A01M 29/12* (2011.01)
  *A61L 9/03* (2006.01)
  *A61L 9/14* (2006.01)
  *B05B 7/22* (2006.01)

(52) U.S. Cl.
  CPC .......... *A01M 7/0003* (2013.01); *A01M 29/12* (2013.01); *A61L 9/032* (2013.01); *A61L 9/14* (2013.01); *B05B 7/22* (2013.01); *A01M 7/0014* (2013.01); *A61L 2209/111* (2013.01); *A61L 2209/13* (2013.01)

(58) Field of Classification Search
  CPC ..... A01M 7/0014; A01M 29/12; A61L 9/032; A61L 9/14
  USPC ......... 239/77, 128, 135, 136, 302, 326, 379, 239/398, 423; 392/395
  See application file for complete search history.

(56) References Cited

U.S. PATENT DOCUMENTS

| | | | |
|---|---|---|---|
| 2,800,457 A | | 7/1957 | Green et al. |
| 2,886,249 A | * | 5/1959 | Sidlow ................ A01M 7/0014 239/77 |
| 3,577,515 A | | 5/1971 | Vandegaer |
| 4,017,030 A | | 4/1977 | Coplan et al. |
| 4,659,013 A | * | 4/1987 | Ledebuhr ................ B05B 3/105 239/77 |
| 5,052,618 A | * | 10/1991 | Carlon ................ A01G 13/065 239/77 |
| 6,322,002 B1 | * | 11/2001 | Forsythe ................ A01N 47/20 239/135 |
| 8,483,553 B2 | | 7/2013 | Tollens |
| 8,833,366 B2 | | 9/2014 | Colombo |
| 9,616,149 B2 | | 4/2017 | Iwaki |
| 2005/0247802 A1 | | 11/2005 | Varanasi et al. |
| 2006/0175425 A1 | | 8/2006 | McGee et al. |
| 2007/0025701 A1 | | 11/2007 | Zhihong et al. |
| 2008/0164337 A1 | | 7/2008 | Brown et al. |
| 2009/0291400 A1 | | 11/2009 | Levy |
| 2011/0049259 A1 | | 3/2011 | Beland et al. |
| 2014/0369895 A1 | | 12/2014 | Turner |
| 2017/0072085 A1 | | 3/2017 | Gruenbacher |
| 2018/0000977 A1 | | 1/2018 | Mitchell |
| 2018/0098573 A1 | | 4/2018 | Yu |

FOREIGN PATENT DOCUMENTS

| | | |
|---|---|---|
| CN | 102648007 A | 8/2012 |
| EP | 1579762 A1 | 9/2005 |
| EP | 1846044 A1 | 10/2007 |
| EP | 2481308 A1 | 8/2012 |
| FR | 2722368 A1 | 1/1996 |
| FR | 3047900 A1 | 8/2017 |
| JP | 05084286 A | 4/1993 |
| JP | 2002-510228 A | 4/2002 |
| JP | 2011-224071 A | 11/2011 |
| WO | 98/58684 A1 | 12/1998 |
| WO | 03092750 A1 | 11/2003 |
| WO | 2008027537 A1 | 3/2008 |

OTHER PUBLICATIONS

Japan Patent Office—Office Action—dated May 30, 2023—see translation.
English translation of first office action for corresponding Chinese application No. 201980041163.5, dated Jun. 2, 2022.
Brazil Patent Office—Search Report and Preliminary Office Action—dated Mar. 22, 2023—see translation.

* cited by examiner

DEVICE FOR DISPERSING IN THE AIR A VAPOR OF A LIQUID SUBSTANCE

The present invention relates to a device for dispersing, in the vapor state in a flow of air, a substance which is in liquid form at ambient temperature. A difficulty in obtaining dispersing of this type generally consists of ensuring that the dispersing is substantially regular over a period of time and in the flow of air, and that the concentration of the substance relative to said flow can be very low. In fact, the problem arises in particular when wishing to diffuse a perfume in a closed area with a large volume, or to diffuse in an open area such as a cultivated field a phytosanitary product which is advantageous for cultivation in said field; the same problem arises when wishing to disperse in an open field a semiochemical product such as a pheromone which can act in order to control insects which are harmful to the cultivation carried out in said field.

Systems have already been proposed which make it possible to obtain slow, continuous release of active liquid substances; these substances are generally liquids used as they are, or absorbed onto different supports; the active ingredient can in particular be located in non-porous polymer matrices, in microcapsules with a polymer envelope (U.S. Pat. No. 3,577,515), in gels (U.S. Pat. No. 2,800,457) or also in hollow fibers (U.S. Pat. No. 4,017,030). The active ingredients are distributed in the ambient air by means of passive diffusion (simple atmospheric evaporation). Unfortunately, the kinetics of release of the active ingredients are affected by ambient factors, which does not make it possible to act efficiently in order to regulate the speed of release of the active ingredients.

In addition, when the liquid substance is constituted by a plurality of compounds which do not have the same evaporation temperatures, the substance is gradually modified during the evaporation, such that the duration of activity of this type of device is uncertain.

Systems have also been proposed for controlling the diffusion of a volatile substance by ensuring controlled evaporation of the active ingredient by means of a heating system; systems have even been proposed with a wick in which heating takes place only of the liquid solution contained in the wick where the evaporation takes place (see in particular patents EP 1579762 and 2481308), or contained in a textile (French patent 2722368).

It has also been proposed to heat a tank of the liquid substance to be vaporized. However, it has then been found that a problem generally arose in obtaining diffusion with a constant composition by means of heating (US patent application 2007/0257016). In all these systems comprising only heating to control the evaporation, it is thus not possible to determine the flow of vapor of the substance precisely at a given moment, nor the period of time during which this flowrate is distributed, without knowing the other variables relating to the evaporation of a substance (including, in particular, the flow of air at the interface, the physical-chemical properties of the substance, and the interaction between the substance and the surrounding surfaces).

In addition, the diffusion of the substance at several points in a treated space can be carried out only by a plurality of devices, each placed at one of the diffusion points used, which does not guarantee regularity of the distributions carried out in the different areas treated, depending on the difference of the variables which are exogenous to the systems and specific to each location. The cost of the systems previously known is therefore not only adversely affected by the consumption of the substance dispersed, but also often by the obligation, in order to obtain acceptable efficiency, of implementing a large number of devices per hectare of surface areas to be treated; the installation of these devices is costly, but also so is their supervision in order to prevent operating incidents from giving rise to localized environmental pollution.

Thus, an objective of the invention is to provide a device which does not have some of the disadvantages previously mentioned.

Certain aspects of the invention start with the concept of proposing a dispersing apparatus, the energy consumption which is low in order to ensure a long period of autonomy.

Certain aspects of the invention start with the concept of proposing a dispersing apparatus which regulates a flow of substance which is distributed by a simple temperature control of the diffuser unit.

Certain aspects of the invention start with the concept of proposing a dispersing apparatus which is particularly suitable for distributing a substance with a high value, with a high level of precision and without losses of substance.

For this purpose, the present invention provides a device for dispersing in the air, in the vapor state, a substance which is in the liquid state at ambient temperature, and is contained in a storage container, the device comprising:
- a ventilation system comprising a duct which opens out into the open air, and is configured to permit the passage of a flow of air into the duct;
- at least one dispensing unit which is designed to be supplied with a liquid substance by the storage container, the dispensing unit comprising micro-ducts forming an outlet which is provided in the duct in order to constitute an area of evaporation of the substance therein;
- a heating unit which is provided on or in the dispensing unit, such as to control a flow of the substance through the dispensing unit.

Within the context of a costly substance, for example if the substance comprises a pheromone which is in liquid form at ambient temperature, it is necessary to avoid wasting some of it. Thus, in this case, it is desirable to introduce a quantity of liquid which is sufficiently small for the flow to take place without formation of drops, but which is nevertheless great enough for the evaporation area to remain wetted permanently, despite the flow of air sent by the ventilation system. This physical phenomenon is governed in cold condition by Jurin's law, and in hot conditions by Darcy's law.

Darcy's law is constituted as follows: $Q=KA\ (\Delta H)/L$, where Q is the volumetric flow rate, K is the hydraulic conductivity, A is the surface area of the section studied, $\Delta H$ is the difference in piezometric heights upstream and downstream from the sample, and L is the length of the sample. The hydraulic conductivity is calculated with the formula $K=k\rho g/\mu$, where k is the intrinsic permeability of the porous medium, $\rho$ is the density of the fluid, g is the gravity acceleration, and $\mu$ is the viscosity of the fluid.

Jurin's law corresponds to the formula $h=(2\gamma\cos(\theta))/(r\rho g)$, where h is the height of the liquid, $\gamma$ is the surface tension of the liquid, $\theta$ is the angle of contact between the liquid and the wall of the micro-ducts, $\rho$ is the density of the liquid, r is the radius of the micro-ducts, and g is the gravity constant.

The aim is to be in conditions where, when cold, K is too low for there to be a flow, i.e. where a so-called "capillary" situation exists, and where, when hot, the flow is sufficient for there to be spreading on the surface, and for the liquid to adhere to the surface. The layer of liquid adhering to the surface modifies ΔH, and a fixed flow is obtained since K has reached a maximal value.

The two most important parameters are thus the viscosity of the fluid and the temperature.

According to one embodiment, cos θ is positive, i.e. the substance has a wetting action on the dispensing unit, which for example is made of ceramic, the density of the liquid is contained between 0.6 and 1 g/cm$^3$, and the radius of the micro-ducts is contained between 5 nm and 1 μm.

In cold conditions, the surface area of the liquid which can be evaporated is thus very small, i.e. sum of the micro-ducts, and liquid held back and cold (therefore dependence on the volatility of the liquid). For pheromones, the evaporation in cold conditions is zero.

The decrease in the dynamic viscosity of the substance as a result of the heat supplied by the heating unit allows the fluid to circulate within the dispensing unit according to Darcy's law, then to be spread on the surface of said dispensing unit. Without the addition of heat, the circulation is stopped, since the sum of the adhesions within the dispensing unit follows Jurin's law. In other words, the flow is permitted through the dispensing unit in hot conditions, but stopped at ambient temperature by the force of adhesion between the fluid and the surface of the dispensing unit.

During the flow, more energy is needed to form a drop which will be detached than to retain the solution within the dispensing unit and the storage container.

This is dependent on two conditions:
1. the dynamic viscosity of the substance must not be too weak in the temperature range which can be achieved by means of the heating unit; and
2. the liquid at the outlet of the tank must be in equilibrium with atmospheric pressure, which can be implemented in several ways. For example, the part without liquid in the storage container is subjected to low pressure.

Alternatively, a system for control of the pressure of the part without liquid of the container ensures this equilibrium.

In the present patent application text, "micro-duct" means a duct, the straight section of which has an area contained between $10^{-4}$ and $10^6$ μm$^2$.

According to one embodiment, the dispensing unit comprises a porous body comprising pores, said pores constituting at least part of the micro-ducts of the dispensing unit.

According to one embodiment, the pores have a diameter contained between 0.01 and 10 μm.

According to one embodiment, the porous body is in the form of a cylinder.

According to one embodiment, the supply of substance is received in a recess.

According to one embodiment, the recess is blind and is provided parallel to the axis of the porous body.

According to one embodiment, the porous body comprises a lug which is provided on an upper part of said body, extends along a longitudinal axis, and is configured to receive the substance.

According to one embodiment, the dispensing unit comprises a peripheral membrane which is provided around the porous body, and is pierced with holes constituting micro-ducts.

According to one embodiment, the porous body has porosity in an inner part of the porous body which is lower than porosity in an outer part of the porous body surrounding the inner part. This makes it possible to control the rate of flow in the porous body with the low porosity, and increase the exchanges with the air with the high surface porosity.

According to one embodiment, the porous body comprises a wick which is made of wood, textile, ceramic or polymer.

According to one embodiment, the heating unit is placed directly on a surface of the porous body.

According to one embodiment, the porous body has at least one recess which accommodates at least part of the heating unit.

According to one embodiment, the dispensing unit comprises a hollow needle which is configured to pierce a cap of the storage container, and/or to displace a membrane which acts as a shutter for the storage container, and bring the substance contained in the storage container to the evaporation surface.

According to one embodiment, the needle is disposed at one of the ends of the porous body. A needle of this type can also be used in combination with a perforable "self-healing" stopper accommodated in the intake of the storage container, i.e. a mass of resilient material which closes resiliently the perforation made by the needle, such that no flowing takes place after the needle is withdrawn.

According to one embodiment, a path from the storage container to an outlet of the micro-ducts in the evaporation area constitutes a micro-duct only on a fraction of a length of the path.

According to one embodiment, the micro-ducts have a cross-section contained between $10^{-4}$ μm$^2$ and $10^6$ μm$^2$, preferably between entre 0.1 μm$^2$ and $10^3$ μm$^2$.

According to one embodiment, the ratio of the inner cross-section of the duct of the ventilation system to a straight outer cross-section of the evaporation area is contained between 1.2 and 625.

According to one embodiment, the device additionally comprises a securing unit, the direction and/or inclination of which can be oriented relative to the duct of the ventilation system, in order to orient the duct relative to the ground when the securing unit is secured on a support.

According to one embodiment, the ventilation system comprises at least one fan which is placed in part of the duct.

According to one embodiment, the ventilation system comprises at least one fan placed in the part of the duct which is opposite its discharge to the open air.

According to one embodiment, the ventilation system comprises openings provided in an end wall of the duct, and adjustable shutters which equip said openings, in order to make it possible to regulate a cross-section of passage of the openings.

According to one embodiment, the device comprises a regulator unit for a flow of air in the duct, which unit is configured to control the fan and/or the shutters, in order to regulate a flow of air in the duct.

According to one embodiment, the flow of air of the ventilation system of the apparatus according to the invention is associated with a regulator unit which can control the turbulence of the flow of air at the evaporation area; the regulator unit can be controlled by at least one temperature sensor which detects the temperature of the flow of air and/or that of the porous body, or by at least one speed sensor which detects the speed of the flow of air.

According to one embodiment, the regulator unit is configured to emit a signal which acts on the speed of rotation of the fan generating the flow of air in the ventilation system, and/or a signal which acts on the adjustable shutters.

According to one embodiment, the flow of air of the ventilation system is contained between 0.2 and 60 m$^3$/h.

According to one embodiment, the duct is equipped with a sensor for the speed and temperature of the flow of air.

According to one embodiment, the piping is equipped with a sensor for the speed and temperature of the flow of air; the control of turbulence of the air, where the substance S is dispersed, is ensured thanks to at least one temperature sensor which detects the temperature of the flow of air and/or that of the porous body.

According to one embodiment, control of turbulence of the air, where the substance is dispersed, is ensured thanks to at least one temperature sensor which measures the temperature of the dispensing unit and/or the temperature of the flow of air.

According to one embodiment, the device also comprises a control device which is configured to control the heating unit according to a set temperature in the dispensing unit.

According to one embodiment, the heating unit comprises at least one electronic board and at least one electrical resistor which is supplied electrically by the electronic board. The electrical resistor can be disposed on said electronic board, or offset from it.

According to one embodiment, the control device is provided on the electronic board.

According to one embodiment, the dispensing unit is equipped with a temperature sensor, for example at a free end.

According to one embodiment, the set temperature is defined according to the substance.

According to one embodiment, the control device is connected to a detector which is configured to detect marking at the storage container indicating the substance contained in the container, and according to said marking the control device determines at least one operating parameter of the device from out of the set temperature, a flow of air, and temporal indications defining a stop/operating cycle. Temporal indications of this type include for example cycle start dates, cycle end dates, cycle durations, inter-cycle duration, etc.

According to one embodiment, the control device comprises a memory which stores a table of values associating substances with set temperatures.

According to one embodiment, the device also comprises a communication module, in order to ensure wired or non-wired communication with a data server, in order to modify the table of values.

According to one embodiment, the invention also provides an apparatus for dispersing in the air, in the vapor state, of a substance which is in liquid form at ambient temperature, comprising:
an aforementioned device; and
at least one storage container which contains the substance and is connected to the dispensing unit.

According to one embodiment, the substance has a viscosity which is variable according to the temperature, said viscosity being such that the substance can not flow through the micro-ducts of the dispensing unit at an ambient temperature lower than a first temperature, and the heating unit is configured to heat the dispensing unit to a second temperature higher than the first temperature, such that a flow of the substance through the micro-ducts of the dispensing unit takes place by capillarity.

According to one embodiment, the substance at the second temperature spreads in the liquid state on a surface of the dispensing unit, which surface is situated in the ventilation system.

According to one embodiment, the heating unit is configured to regulate a flow of the substance through the dispensing unit by modifying a viscosity of the substance without vaporizing the substance.

According to one embodiment, the second temperature is selected such that the flow of the substance takes place at a flow rate which is sufficiently low to prevent the formation of drops becoming detached from the dispensing unit, and sufficiently great for the evaporation area to remain permanently wetted despite the flow of air sent by the ventilation system.

According to one embodiment, the storage container has a discharge orifice which is connected to the dispensing unit, and is oriented downwards when the apparatus is in a position of use.

When the apparatus is not being used, i.e. before the container is connected to the dispensing unit, or after it has been disconnected from the dispensing unit, a storage container of this type can be provided with a stopper placed on the discharge orifice.

According to one embodiment, the storage container does not have an opening other than the discharge orifice, said storage container containing a gaseous phase which occupies at least 20% of the volume of the storage container, as well as the liquid substance.

According to one embodiment, the storage container comprises an outer tank and an inner tank which is accommodated in the outer tank, the inner tank being connected to the dispensing unit via the discharge orifice, and having a vent which is connected to the atmosphere at an end opposite the discharge orifice, an orifice for communication between the outer tank and the inner tank being provided in the vicinity of the discharge orifice, the outer tank not having an opening other than the communication orifice.

According to one embodiment, the storage container is fitted removably in the device, and is configured such as to be able to be removed from the device without loss of substance.

According to one embodiment, the storage container is fitted in the device by being screwed or snapped in.

According to one embodiment, the dispensing unit has a first surface which faces towards the storage container, and is provided with a seal ensuring a sealed connection between the dispensing unit and the storage container, and a second surface which is provided in the ventilation system.

According to one embodiment, the storage container comprises a seal which is provided around the discharge orifice such as to ensure a sealed connection between the storage container and the dispensing unit.

According to one embodiment, the storage container comprises an alveolar retention unit which is provided in the container in a manner adjacent to the discharge orifice, in order to limit a flow of the substance.

According to one embodiment, the heating unit and the storage container are disposed on both sides of the dispensing unit.

According to one embodiment, the alveolar retention unit comprises a material selected from between a felt, for example a wool felt, and a melamine foam.

According to one embodiment, a connection between a storage container and its associated dispensing unit is ensured by means of piping equipped with a stop solenoid valve at the outlet of the container.

According to one embodiment, a distribution regulator means is inserted between the storage container for the substance and the dispensing unit.

According to one embodiment, the distribution regulator means is a valve with adjustable opening.

According to one embodiment, the valve has only two adjustment positions, i.e. opening or closure.

According to one embodiment, the flow regulator means is a pump which is supplied electrically.

According to one embodiment, the substance has a boiling temperature contained between 30° C. and 400° C. at atmospheric pressure.

According to one embodiment, the substance has a viscosity greater than 1 cPa·s at 25° C., for example greater than 8 cPa·s at 25° C., and less than 1 cPa·s at 60° C.

According to one embodiment, the substance is a solution comprising at least one compound taken from the group formed by odiferous agents which can be used for people or animals, semiochemical substances, cosmetic agents, essential oils, perfumes and phytosanitary and agricultural agents.

According to one embodiment, the odiferous agents which can be used for animals are selected from amongst fatty acids or the esterified form of said fatty acids, such as methyl oleate, methyl palmitate, dimethyl azelate, and dimethyl pimelate.

According to one embodiment, the substance is a solution which contains at least one semiochemical substance, at least one pheromone, an allomone or a kairomone of natural or synthetic origin.

According to one embodiment, the substance is a solution containing at least one pheromone which is or is not sexual, an allomone, a synomone or a kairomone, designed to provoke a positive or negative response relative to the species concerned, the behavioral result of which can be sexual confusion, confusion of another kind, sexual attraction, attraction of another kind, repulsion of any kind, in arthropods, including arachnids, or including hexapods, which includes in particular insects, including harmful insects.

According to one embodiment, the substance is a solution containing at least one pheromone or a sexual pheromone, an allomone, a synomone or a kairomone designed to provoke a positive or negative response relative to the species concerned, the behavioral result of which can in particular be pacifying, relaxation, mood elevation, or intimidation, in the classes mammalia and ayes.

According to one embodiment, the substance comprises a solvent selected from amongst isopropyl myristate, dipropylene glycol, monomethyl dipropylene glycol ether, and an isoparaffinic hydrocarbon, for example an isoparaffin L or P or N or V.

According to one embodiment, the apparatus comprises a plurality of storage containers each containing a substance in liquid form, or a plurality of substances in liquid form which are miscible with one another.

According to one embodiment, all or part of the assembly of the storage containers is supported on the exterior by the duct of the ventilation system.

According to one embodiment, all or part of the assembly of the storage containers can be supported on the exterior by the duct of the ventilation system or its extension piping.

According to one embodiment, each storage container is associated with a porous body of the dispensing unit, the assembly of the porous bodies being placed in the interior of the duct of the ventilation system, and being disposed with offsettings of the porous bodies in a longitudinal direction of the duct.

According to one embodiment, the assembly of the porous bodies is placed in the interior of the duct or the piping of the ventilation system, and can be disposed with appropriate offsettings of the porous bodies, in order to prevent an obstruction impeding the passage of the flow of air.

The invention also provides a method for use of the device or the apparatus, in which the direction and/or inclination of the axis of the duct of the ventilation system is oriented so as to reach an area to be treated.

In order to make the present invention better understood, a description will now be provided purely by way of non-limiting illustration of embodiments represented in the appended drawings.

In the embodiments described hereinafter, it is envisaged to diffuse in a flow of air substance constituted by a pheromone solution in accordance with the following composition:

87% by weight of (8E,10E)-dodeca-8,10-dien-1-ol, known by the name of Codlémone, a pheromone which is associated with *Cydia pomonella* (lepidoptera, tortricidae); and 13% by weight of dodecane-1-ol. This solution is known by the brand name RAK3®.

The intake temperature with boiling at atmospheric pressure of the solution of Codlémone is approximately 270° C., and the viscosity at ambient temperature, i.e. 25° C., is approximately 8 cPa·s and 1 cPa·s at 60° C.

In the solution, it is possible to substitute the Codlémone by the pheromone with the formula (7E,9Z)-Dodeca-7,9-dienylaceteate, with the brand name RAK2®, the boiling temperature of which is approximately 300° C. The viscosity of the solution remains close to that of the Codlémone solution. The RAK2® pheromone can also be used pure (100% by weight).

Alternatively, the substance can be constituted by rapeseed oils, the viscosity of which is 7.78 cPa·s at 20° C. and 2.57 cPa·s at 50° C. The boiling temperature is approximately 150° C.

Figure 1:
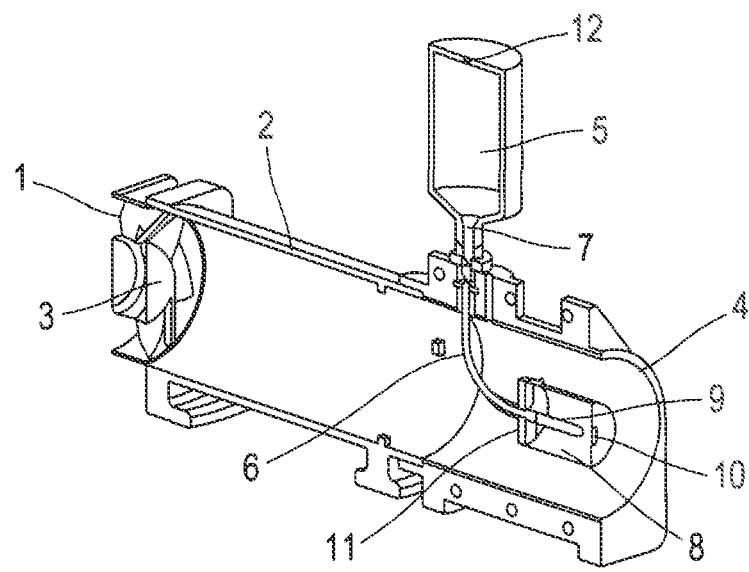
FIG. 1 represents a first embodiment of the apparatus according to the invention in a cut-away view in perspective.

According to a first embodiment illustrated in FIG. 1, the apparatus is constituted by a ventilation system comprising an electric fan 1, the outlet from which is placed on the axis of a cylindrical duct 2, with the flow of air pulsed by the electric fan 1 passing through a grid 3. The elements which constitute this grid can be profiled in order to act on the flow of air in the interior of the duct 2. In the extension of the duct 2, piping 4 has been put into place with the same diameter as the duct 2, to which it is connected. The piping 4 opens into the open air on the side opposite its area of connection to the duct 2.

Externally, the piping 4 supports a storage container 5, which is designed to receive the substance, the diffusion of which is to be ensured in the flow of air pulsed by the electric fan 1. The storage container 5 comprises an outlet provided in its wall, which outlet is supported on the piping 4; this outlet supplies a pipe 6 with an inner diameter of approximately 800 µm; the pipe has a length of approximately 3 cm; the intake of the pipe 6 is equipped with a solenoid valve 7 which allows the system to be stopped, in an emergency in particular. The pipe 6 connects the storage container 5 to a porous cylindrical body made of ceramic 8, which comprises a blind axial cylindrical recess 9, in the interior of which the end of the pipe 6 is engaged in a sealed manner. On the end face of the porous body 8 where the pipe 6 is not introduced, a tablet-thermometer 10 is placed, which can measure and transmit the temperature of the porous body 8. On its face which is opposite the one where the tablet-thermometer 10 is located, this cylinder 8 supports a heating unit 11. The porous body 8 is made of alumina, and has pores with a diameter of 100 nm and regular porosity of 40%.

On the surface of the storage container 5, electronic marking 12 is put into place, which makes it possible to identify the solution of Codlémone placed in the container 5. This electronic marking is in the form of a label comprising a radio-identification chip which is also known as an RFID (radio frequency identification) chip. In the high part of the container 5, an opening which is sealed against the liquid has been provided, thus permitting the retention thereof in the interior of the container at atmospheric pressure. The porous body 8 is selected according to the substance to be diffused, in this case Codlémone. It is possible for the porous body 8 and the pipe 6 to be constituted in a single piece and/or to be integral with one another.

The information relating to the characteristics specific to the substance, to the characteristics selected for the porous body 8, and/or to the temperature of the porous body 8, is information which is sent to an electronic controller (not represented), which carries out automatically the few adjustments which are advantageous for adjustment of the ratio of the flows of air to the required value, i.e. the ratio between the flow of air without the electric fan and the flow of air generated by the fan, and the temperature of the porous body 8 which quantifies the evaporated flow of the pheromone solution in the gaseous flow produced by the apparatus according to one of the variants of the control method described.

The substance is drawn into the pipe 6 by a capillary pumping force generated by the fact that the substance is displaced in micro-ducts, the walls of which the substance wets because of its surface tension. It will be appreciated that the materials used are sufficiently neutral not to downgrade the mixture in the long term, and for the surface tensions not to be modified. The capillary force is created by the nature of the surface, which is constituted by channels or pores sufficiently narrow to generate capillary traction; the liquid wets the materials of the pipe 6 and the porous body 8. The liquid thus laps the end of the pores of the porous body, the assembly of which constitutes the evaporation surface thus situated on the periphery of the porous body 8.

The force of capillary attraction and retention must permit lapping of the liquid on the end of the pores of the evaporation surface; nevertheless, this lapping must take place without however permitting uncontrolled spreading on the evaporation surface via the forces caused by the fields of gravity (terrestrial attraction hydrostatic pressure of the column of liquid potentially present) or by the static forces of attraction generated by the interactions between the solution and the remainder of the surface of the wick. This capillary traction exists only by means of renewal of this final volume block (the section/cylinder of liquid at the end of the pore). This volume is renewed by the evaporation, and is governed by the equilibrium of the concentrations of the liquid and gaseous molecules at the liquid and gas interface according to a value which is specific to each solution, and is dependent mainly on the temperature (at atmospheric pressure), i.e. the pressure of saturating vapor. The increase in the temperature of the solution to be evaporated gives rise to an increase in the pressure of saturating vapor, and thus to displacement of the equilibrium of the concentrations of liquid and gaseous molecules at the interface towards the gaseous molecules: evaporation takes place until equilibrium is established once more. If the gaseous phase is mobile, the equilibrium is never achieved, and the evaporation continues until the liquid phase is used up. The more the gaseous phase is mobile (and tends to discharge the molecules in gaseous phase more quickly), the more the evaporation is rapid.

It has been found that, in a system of the type previously described, the kinetics of evaporation are multiplied by a factor contained between 1 and 10 when going from 0 to 24 m/s of ventilation; in addition, if the liquid goes from 20° C. to 70° C., the kinematics of evaporation are increased by multiplying them by a factor contained between 20 and 100.

The parameters of the system described can be adjusted by acting on the fan 1 (action on the flow of air), and/or by acting on the heating unit, in this case an electric heater 11, also known as a resistor, placed on the evaporation surface. The measurement which can be made by means of the thermometer 10 makes it possible to adjust the intensity or the time of activation of the electric heater, in order to obtain the required temperature of the evaporation surface. At the free end of the piping 4, it is also possible to provide agitators for the flow of air blown, or convectors in order to adjust the surface on which the substance is dispersed.

Figure 2:
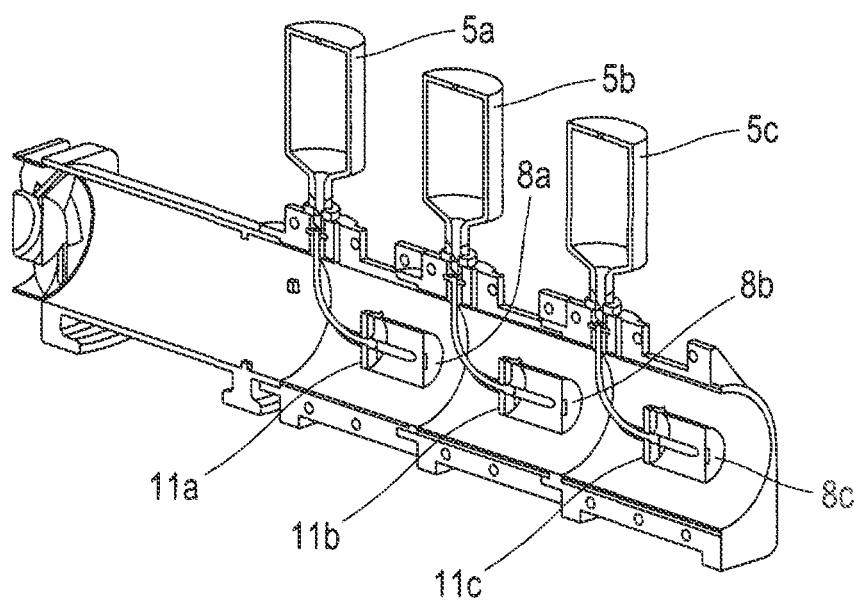
FIG. 2 represents a view in perspective similar to FIG. 1 of an apparatus according to a variant embodiment which can disperse a plurality of liquids in the same flow of pulsed air.

FIG. 2 represents a variant embodiment of the apparatus, in which said apparatus is equipped with three distinct storage containers 5a, 5b, 5c, respectively associated with dispensing units constituted by porous bodies 8a, 8b, 8c, which are altogether similar to the porous body 8 previously described for the variant in FIG. 1. With each porous body, there is associated an electric heater 11a, 11b, 11c, placed on the outer surface of the porous body. The porous bodies 8a, 8b, 8c, are offset relative to one another in the blowing path of the air, which is defined by the piping 4, such that the fact of having increased the number of porous bodies avoids constituting an obstruction which impedes the passage of the air. In FIG. 2, the porous bodies 8a, 8b, 8c are placed in series, however according to a variant embodiment not represented, the porous bodies can be disposed in parallel.

Whether an apparatus of the type in FIG. 1 or FIG. 2 is involved, the user of the apparatus will therefore act on the functioning by action on the temperature of the porous body/bodies 8, 8a, 8b, 8c, by action on the resistors associated with the porous bodies, and by action on the ventilation speed (electrical supply of the fan 1). All of these functions can be easily grouped together on a controller (not represented), and the apparatus according to the invention thus has functioning which can be made entirely automatic, with the electronic marking 12 making it possible to differentiate the liquids to be diffused. The controller can have a connection antenna which permits transfer of the information from the controller to the user, or conversely. Alternatively, the functioning can be controlled remotely by the user via a smartphone for example.

Figure 3:
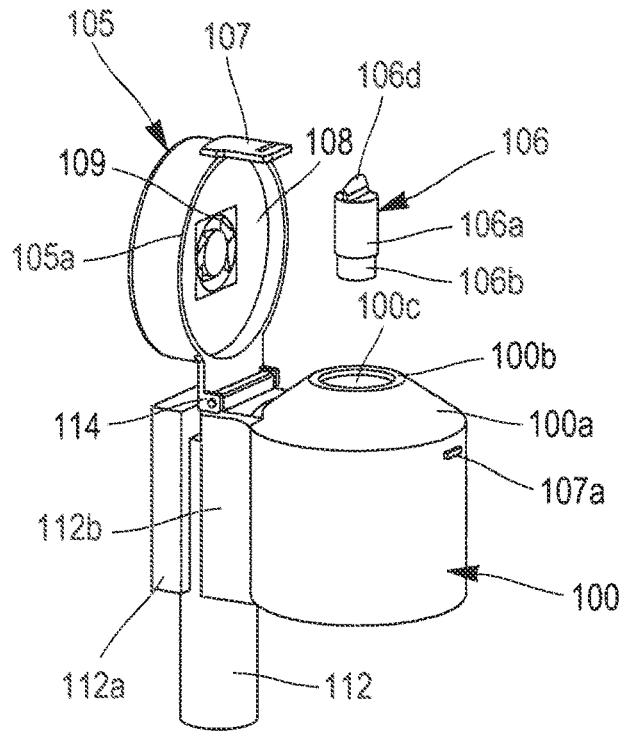
FIG. 3 represents an exterior view in perspective of an apparatus according to a second embodiment.

According to a second embodiment illustrated in FIG. 3, the apparatus comprises a cylindrical housing with a vertical axis designated by 100 as a whole; said housing is supported at approximately 1.50 m from the ground by a foot 112, on the top of which it is coupled mechanically by two jaws 112a, 112b which can be clamped; the jaw 112b is integral with the housing 100. The upper part of the housing 100 has the form of a truncated cone 100a, the upper border 100b of which delimits a circular opening 100c on the side opposite the ground. The frustoconical wall 100a can be covered by a cover which is designated by 105 as a whole; the cover 105 is articulated by means of a shaft 114 on the jaw 112b; the shaft 114 is perpendicular to the shaft of the foot 112.

When the cover 105 is open as represented in FIG. 3, it opens up the orifice 100c totally, and makes it possible to introduce a cylindrical storage container designated by 106 as a whole into the housing 100. The container 106 shuts in the liquid substance, the diffusion of which is to be carried out in the vapor state in the ambient air. The container 106 comprises two parts: the upper part 106a is made of strong plastic material, whereas the lower part 106b comprises a wall which is easily perforable. In its upper part, the container 106 is provided with a pre-emption tab 106d.

Figure 4:
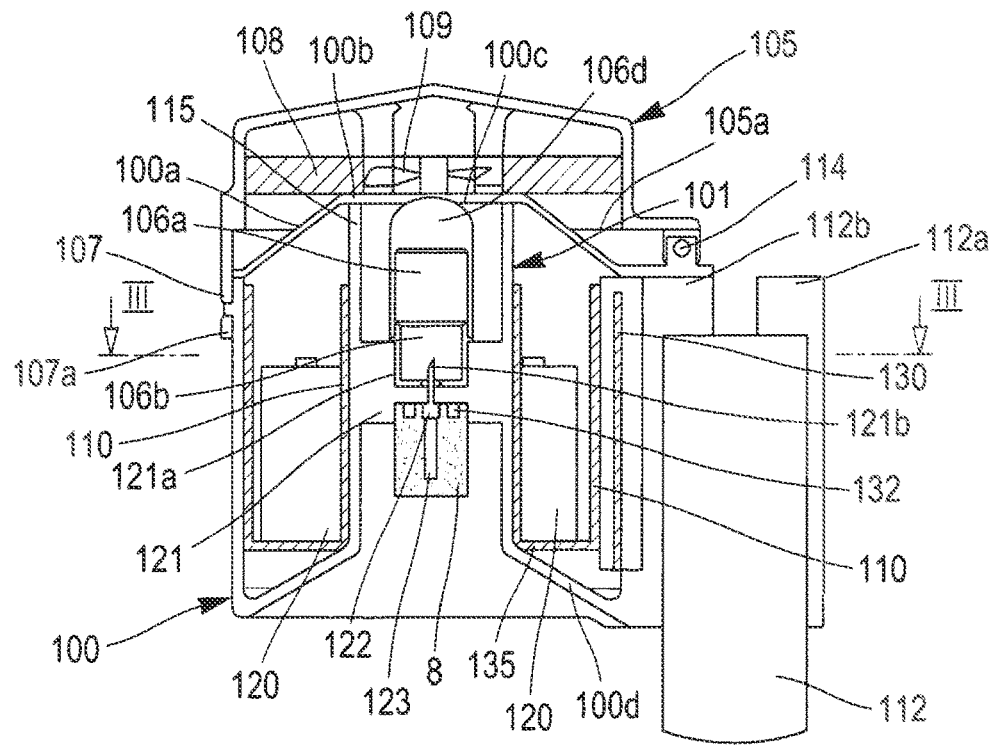
FIG. 4 represents a cross-section of the apparatus in FIG. 3 along the cross-sectional plane II-II positioned in FIG. 5.

With reference to FIG. 4, when the cover 105 is in the closed position, the position of the cover relative to the housing 100 is maintained by means of a closure element 107 which is integral with the cover 105. The closure element 107 cooperates with an appropriate snapping-in portion 107a of the housing 100. An element of the cover 105 is supported on the part 106a of the container 106, in order to apply the base of the part 106b against the base of a receptacle 121, which will be described hereinafter. When the cover 105 is in the closed position, its lower border 105a is in line with the truncated cone 100a, which forms the high part of the housing 100; however, the border leaves a free space between the bottom of the cover 105 and the truncated cone 100a. In the base of the cover 105, a filter 108 with the form of a circular flat collar is put into place, with the same axis as the cover 105; when the cover 105 is closed, the axis of the collar-filter 108 becomes that of the housing 100. In the central recess provided in the collar-filter 108, a fan component 109 is put into place, which is supplied electrically by a conductor (not represented) supported by the wall of the cover 105. The air is aspirated by the fan 109 through the space provided between the cover 105 and the truncated cone 100a; it then passes through the collar-filter 108 and comes in line with the circular opening 100c. The housing 100 comprises in its interior a structure 101 connecting the truncated cone 100a of its upper part to a frustoconical widening 100d, which constitutes the lower base of the housing 100. Between the part with the smallest cross-section of the widening 100d and the part with the smallest cross-section of the border 100b of the orifice 100c, a cylindrical wall 115 is provided, in the interior of which, substantially halfway up the height, a cross-piece 121 is provided, which is designed to support the container 106 in its central part. The central part of the cross-piece 121 comprises a receptacle 121a which is open in the direction of the cover 105; the part 106b of the storage container 106 is positioned in this receptacle. The base of the receptacle 121a comprises a perforator unit 121b in relief, constituted by a needle 133, the end of which is cut beveled: this needle can perforate the base of the part 106b of the storage container 106 when the container is positioned in its planned location 121a by an operator. The needle 121b defines a capillary passage 134 in the direction of a porous body 8 with a cylindrical form, constituted by sintered alumina. The porous body 8 has pores with a diameter of 100 nm and regular porosity of 40%. The needle 121b is plunged into a starter hole 122 in a sealed manner, and is retained by adhesion, and it supplies a blind duct 123 provided along the longitudinal axis of the porous body 8.

Figure 5:
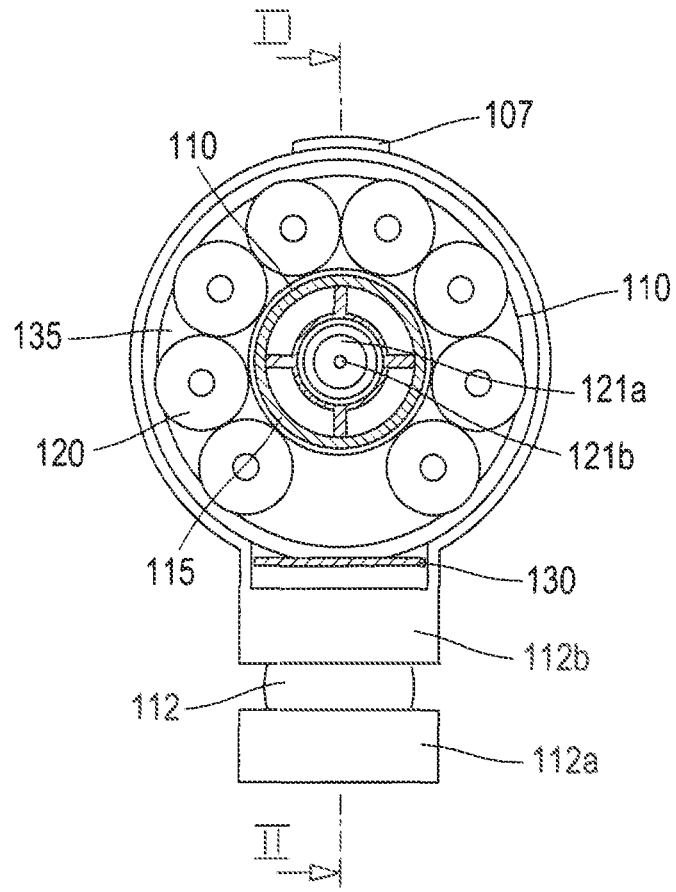
FIG. 5 represents a view in cross-section along horizontal plane positioned along the line in FIG. 4.
Figure 6:
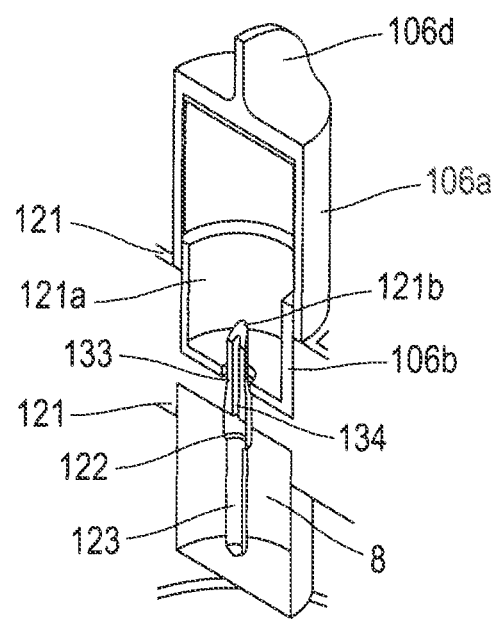
FIG. 6 is a simple detail diagram of the assembly of the perforator unit integral with the porous body.

Around the central part of the structure which has just been described, and is designated generally by the reference 101, there is another cylindrical wall 110 coaxial to the cylindrical wall which delimits the area of the storage tank 106, and extends around the porous body 8. This cylindrical wall 110 is integral with a base, which constitutes a collar 135 connecting the two cylindrical walls 110 and 115 to one another; on this collar 135 electric batteries 120 are disposed, regularly distributed around the axis of the housing 100; the assembly 110, 115, 135 constitutes a barrel, as can be seen clearly in FIG. 5. The batteries 120 supply the energy which is necessary for the functioning of the apparatus according to the invention.

These batteries are connected to a control board 130, which is accommodated in the part of the jaw 112b positioned tangentially relative to the barrel of batteries. The board 130 is connected electrically, firstly to the motor of the fan 109, and secondly to heating units 132 which are inserted in the porous body 8, in particular on the face thereof which is inserted in the interior of the radial arms of the cross-piece 121.

Figure 7:
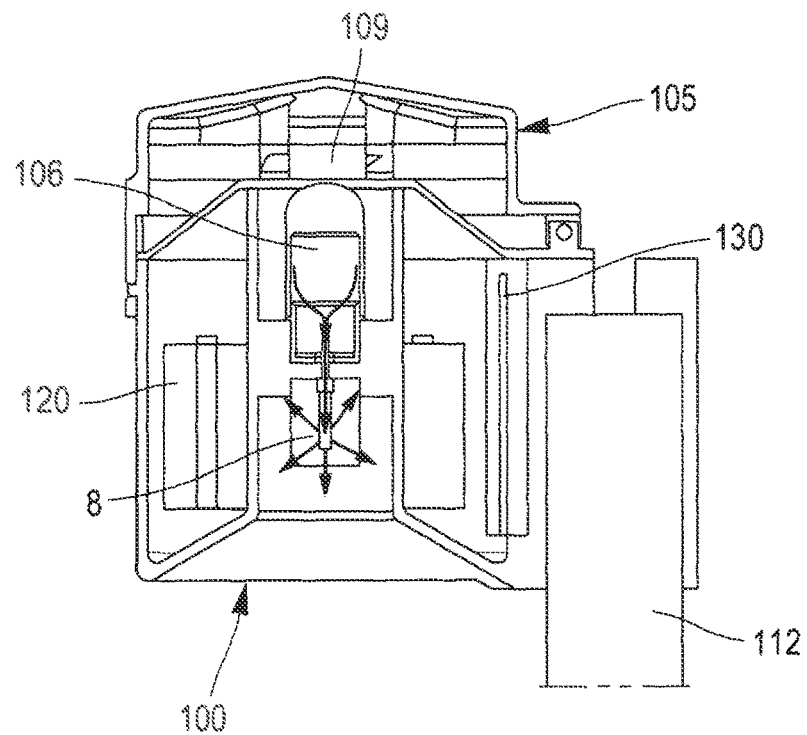
FIG. 7 represents the flow of the substance in the apparatus in FIG. 4.

In the apparatus which has just been described, the Codlémone solution which is introduced by the storage container 106 is distributed as soon as the cover 105 gives rise to perforation of the container 106b by the perforator element 121b, through the porous body 8, the area of evaporation of which is the free surface, as indicated by the arrows in FIG. 7.

Figure 8:
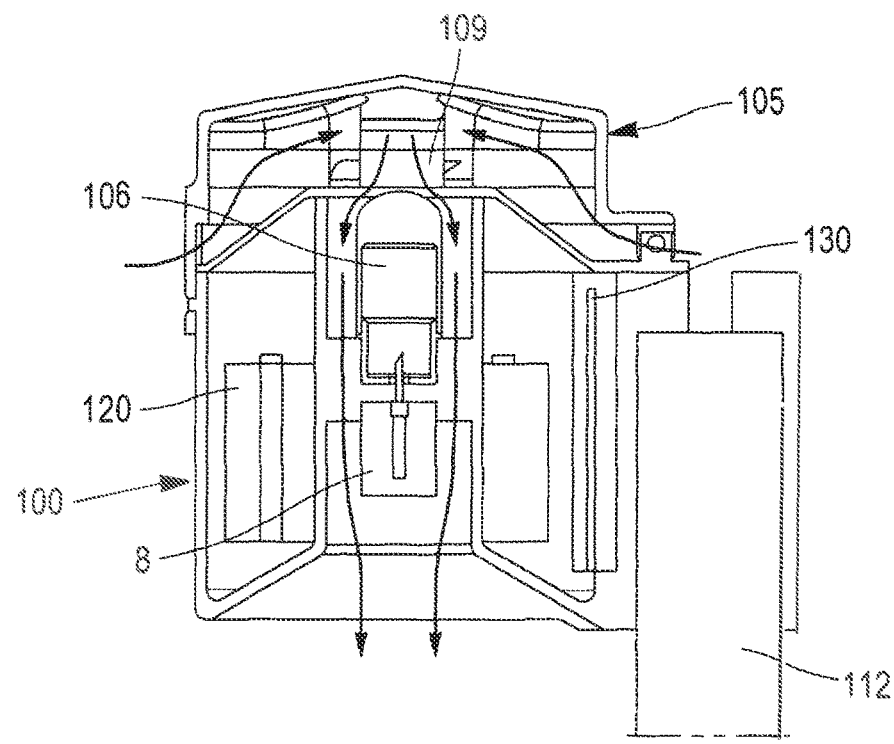
FIG. 8 represents the flow of the air in the apparatus in FIG. 4.

With reference to FIG. 8, the air which ensures the evaporation penetrates below the cover 105, in which it is aspirated by the fan 109; this air flows around the storage container 106, crosses the cross-piece 121, and is discharged to the exterior by passing via the frusto-conical widening 100d, after having been charged with the vapor of the Codlémone solution at the evaporation area, which constitutes the free surface of the porous body 8. The flow of the air is shown by the arrows.

The flow of air and the temperature of the heating body are regulated by the control board 130.

Preferably, the substance and the porous body 8 have physical properties which permit regulation of the flow by temperature control in the porous body 8.

In particular, according to a preferred embodiment:
no substantial flow takes place at ambient temperature, i.e. for example in a temperature range contained between 0° C. and 30° C.;
the flow and the evaporation take place above a set temperature T which can be reached by the heating units 132.

The control board 130 controls the heating units 132 according to a control program which is stored in its memory. This program defines for example the times of start and end of distribution, the set temperatures, the flows of air (if there is forced ventilation), etc.

According to an embodiment not represented, the solenoid valve of the first and second embodiments can be replaced by a manual valve. It can also be eliminated in each of the embodiments.

Figure 9:
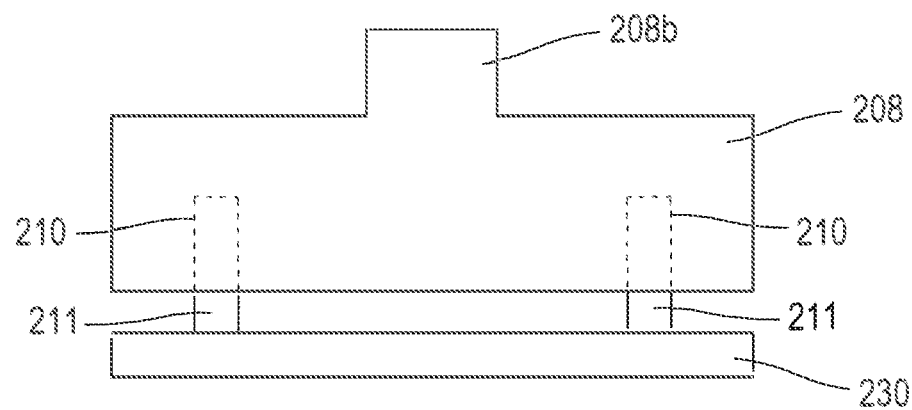
FIG. 9 represents a porous body with the heating units according to another embodiment.

A variant embodiment of the porous body is illustrated in FIG. 9. The porous body 208 has a cylindrical form which is surmounted by a lug 208b. This lug will make it possible to conduct the substance to the remainder of the porous body when the cartridge is fitted in the apparatus. On the face of the porous body opposite the one which supports the lug, two recesses 210 are provided in order each to receive a heating unit 211. The heating units 211 are electrical resistors which are supplied with power by an electrical circuit 230.

According to this variant embodiment, the porous body can equally well have regular or irregular porosity. In this last case, the open porosity is 25% at the core and 45% on the surface. This will then be a porous body, the open porosity of which, i.e. the volume of pores per unit of volume of the porous body, increases going from the core towards the evaporation surface. Thus, precedence is given to the greatest possible spreading on all of the surface of the porous body at the outlet from the pores, and the mechanical intactness of the porous core is preserved with a denser core.

Figure 10:
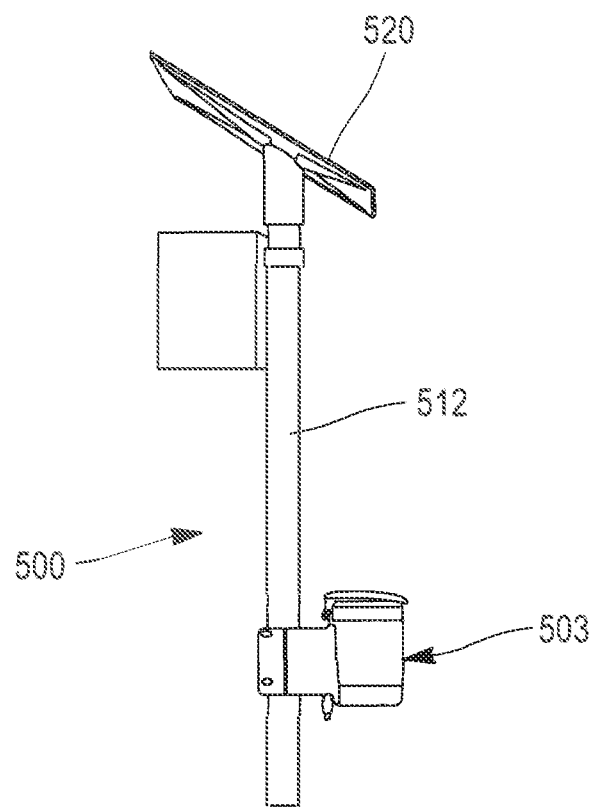
FIG. 10 represents an exterior view in perspective of an apparatus according to a third embodiment.

A third embodiment of the apparatus is illustrated in FIG. 10. The apparatus 500 comprises a housing with a vertical axis 503; said housing is supported at approximately 1.50 m from the ground by a foot 512, at the top of which solar panels 520 are secured in order to supply the apparatus 500 with energy. The housing 503 is mechanically attached to the foot by two jaws 512a, 512b which can be clamped; the jaw 512b is integral with the housing 503. Preferably, an articulation (not represented) is provided between the jaw 512b and the housing 503, in order to permit adjustment of the orientation of the housing 503.

Figure 11:
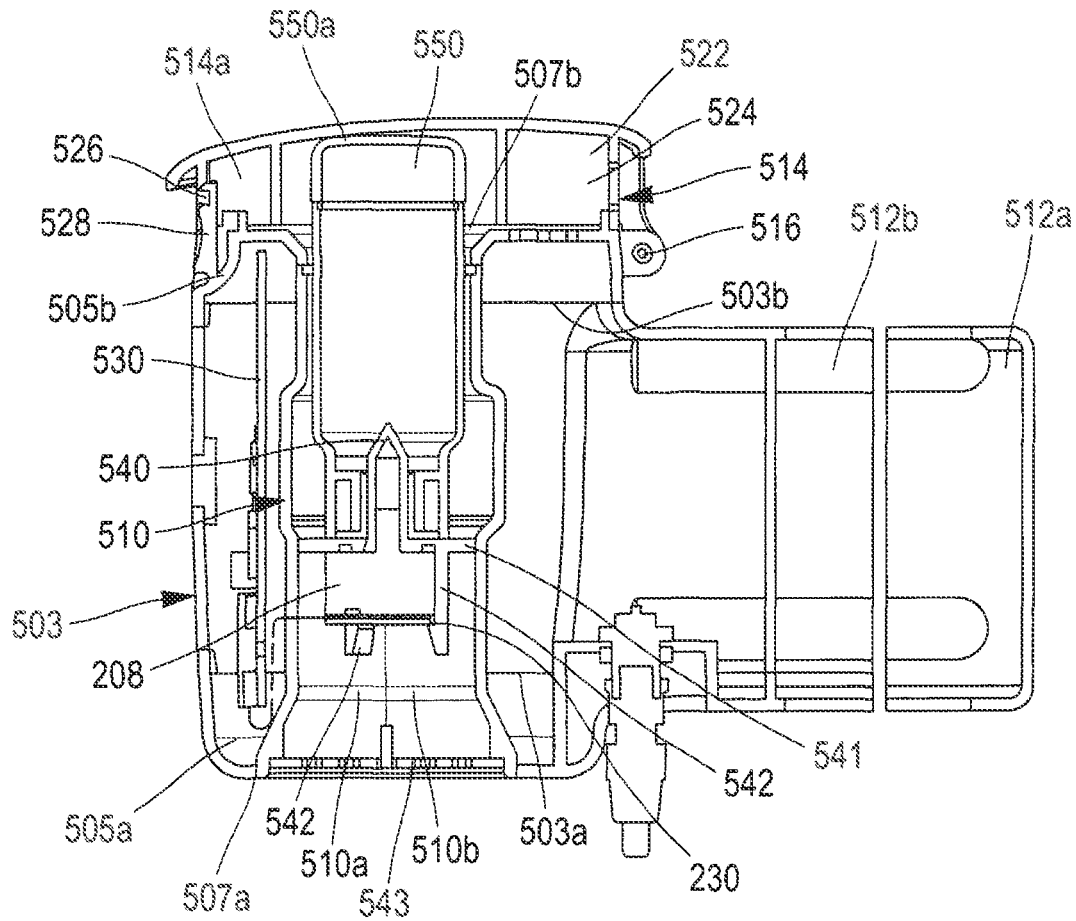
FIG. 11 represents a sectional view of the apparatus in FIG. 10.

With reference to FIG. 11, the housing 503 has the form of a cylinder with a square directrice. The upper border 503b of the housing delimits a square upper opening with rounded corners on the side opposite the ground, and the lower border 503a of the housing delimits a square lower opening with rounded corners on the side facing the ground. The upper opening is covered in a sealed manner with an upper part 505b, and the lower opening is covered in a sealed manner with a lower part 505a. The upper and lower parts each comprise a central opening 507a, 507b, with the two central openings having the same central axis.

The upper part 505b can be covered by a cover 514; the cover 514 is articulated by means of a shaft 516 which is perpendicular to the shaft of the foot 512.

When the cover 505 is open, it opens up the central opening 507b totally, and makes it possible to introduce a cylindrical storage container, designated by 550 as a whole, into the housing 503. The container 507 contains the pheromone solution, the diffusion of which is to be ensured in the vapor state into the ambient air.

When the cover 514 is in the closed position, as illustrated in FIG. 11, the position of the cover relative to the housing 503 is maintained by means of a closure element 526 which is integral with the cover 514. The closure element 526 cooperates with an appropriate snapping-in portion 528 of the upper part 505b. An element of the cover 514 is supported on the part 550a of the container 550, in order for the needle 540 to pierce the stopper of the container 550, and retain the container in position in the housing. When the cover 514 is in the closed position, its lower border 514a is in line with the lateral walls of the upper part 507b, which forms the high part of the housing 503. The lower border 514a has an opening 522, such as to allow air to circulate in the housing 503. In order to prevent dust from entering via the opening 522, a filter 524 is placed behind the opening.

The housing 503 also comprises a hollow cylinder 510 formed by two identical hollow half-cylinders 510a, 510b. When they are assembled, these two half-cylinders sandwich the porous body 208 which is surmounted by a needle 540 and is supported on the heating unit, the electrical circuit 230 of which is represented. The needle is secured on the porous body by means of clips 542 extending longitudinally from a collar 541 to the base of the needle 540. When they are assembled, the two half-cylinders also sandwich a filter 543 at their base, and two fans (not represented) at the junction of the lateral walls of the half-cylinders. The assembly formed by the needle and the porous body is retained by a groove in the interior of the walls of the cylinder, with the groove receiving the collar 541. The filter is secured on the cylinder in an identical manner Finally, the cylinder 510 is retained between the upper 507b and lower 507a parts in line with the openings of these parts 507b, 507a, with the upper and lower parts sandwiching the cylinder 510.

Figure 12:
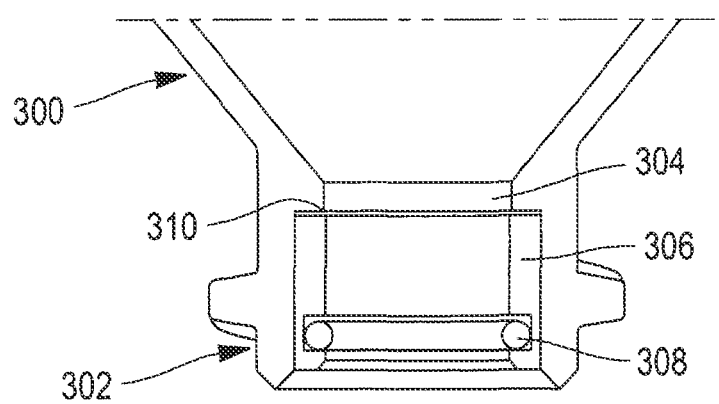
FIG. 12 represents a storage container, a sealing area of which is formed by a seal.

The solar panels are connected to a control board 530, which is accommodated in a receptacle between the walls of the housing 503, the hollow cylinder 510 and the upper and lower parts. The board 530 is connected electrically, firstly to the fans, and secondly to the heating unit, the electrical circuit 230 of which is represented. With reference to FIG. 12, the storage container 300 has an opening 304 in its lower part 302. The opening is equipped with a stopper, in order to prevent the substance from flowing when the storage container is not being used. This stopper is constituted by a ring 306 which supports an O-ring seal 308 and a membrane 310 glued onto the ring. The membrane comprises a sheet of aluminum which is sealed and perforable or displaceable in the manner of a shutter.

The storage container can be designed to be removable, in particular because this facilitates the change of storage container at a lower cost. According to one embodiment not represented, the stopper then also comprises a shutter which is configured to close when the storage container is removed from the apparatus. In this case, it is impossible to remove the storage container until all of the porous body is impregnated with the substance contained in the porous body.

Figure 13:
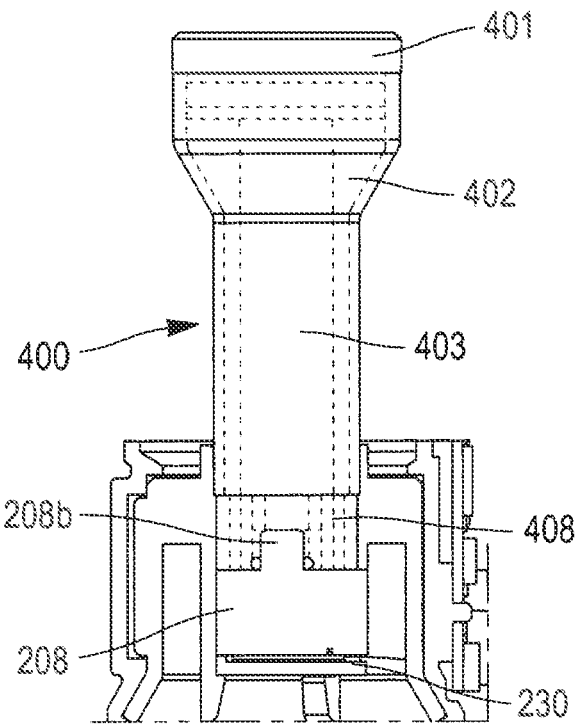
FIG. 13 represents a storage container, a sealing area of which is formed by a sponge.
Figure 15:
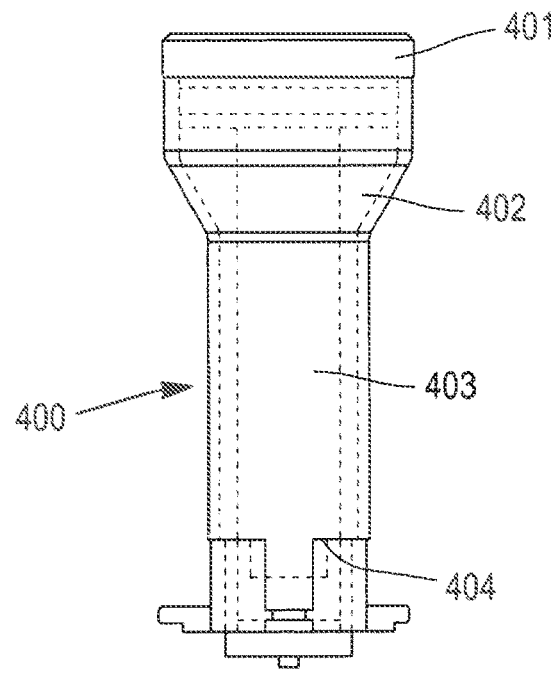
FIG. 15 represents a storage container according to an embodiment with double tanks.

As an alternative to the use of a needle and a shutter, the storage container can contain a sponge as illustrated in FIGS. 13 and 15. The lug 208b of the porous body comes into contact with another porous body forming a retention unit, in this case a sponge 408, which is contained in the storage container and constitutes one of the free ends thereof. The sponge 408 is then compressed by the porous body 208 in order to ensure good contact. The transfer of a porous body 208b to the retention unit by contact and by capillary traction can take place. The storage container is then removable, and the liquid will not flow from the container when the contact with the porous body 208b is broken, and in the same manner as during functioning in cold conditions (ambient temperature) the liquid will not flow from the porous body 208. This sponge 408 is generally made of wool felt or melamine. To conclude, the sponge is preferably flexible and slightly compressible by the porous body 208, in order to ensure the contact.

In general, the storage container is retained on the apparatus by pressure, for example by means of clips, or by screwing of the head of the storage container. In all cases, the contact between the storage container and the porous body is sealed as a result of the presence of a seal.

Figure 14:
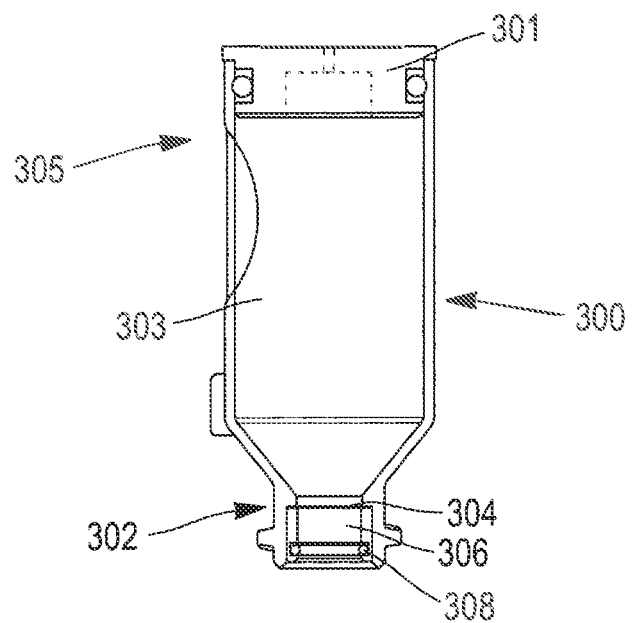
FIG. 14 represents a storage container according to an embodiment which is totally closed.

In order for the adhesion of the substance on the porous body 208 to be sufficient, one of the parameters to be controlled is the pressure in the interior of the storage container. In fact, if the storage container is open to the open air, the adhesion of the substance will never be sufficient to compensate for the force of gravity being exerted on the liquid. It is therefore necessary to control this force of gravity. Two types of storage containers can be used. The first type of the storage container is a tank which is totally closed except at one of its ends which is in contact with the porous body. This type of storage container is illustrated in FIG. 14. The storage container 300 comprises a single tank 303 which is surmounted by a sealed closure 301. The lower part 302 of the storage container comprises a stopper as described in FIG. 12. For each drop which flows towards the porous body, the low pressure increases in the high part 305 of the storage container, i.e. the part where there is no liquid or no longer any liquid. In order for the flow to take place totally, when the storage container 300 is put into place in the apparatus, it is necessary to leave a sufficiently large volume of liquid in the tank, i.e. a volume of approximately 40% relative to the total volume of the tank. Thus, the low pressure will gradually increase and prevent the free flow, but it will never be sufficient to block all of the flow towards the surface of the porous body.

With reference to FIG. 15, the storage container 400 comprises an outer tank 402 which is totally closed except at its end which is in contact with the inner tank 403. The inner tank 403 is surmounted by a vent 401 at its upper end, with the event permitting equilibrium of the pressures between the exterior air and the interior of the inner tank. The inner tank 403 is in contact with the porous body at its lower end. Thus, for each drop which flows towards the porous body, the inner tank 403 is put into equilibrium by its vent 401, and gives rise to a decrease in the level. By the principle of communicating vessels via the junction 404 between the two tanks, the outer tank 402 fills the inner tank 403, but then the low pressure of the outer tank 402 increases in the part of the tank where there is no liquid or no longer any liquid. Thus, the equilibrium of the inner tank 403 is obtained by means of the low pressure of the outer tank 402. However, the inner tank 403 can lose this equilibrium by means of its vent 401 and the traction applied by the porous body of the dispensing unit. In order for the flow to be able to take place normally, when the storage container 400 is put into place in the apparatus, the outer tank 402 is completely filled with the substance.

The retention unit described above can also be used in the storage container 400. In the storage container 400, the retention unit, which for example is made of sponge or alveolar foam, can occupy all or part of the lower tank 403.

Figure 16:
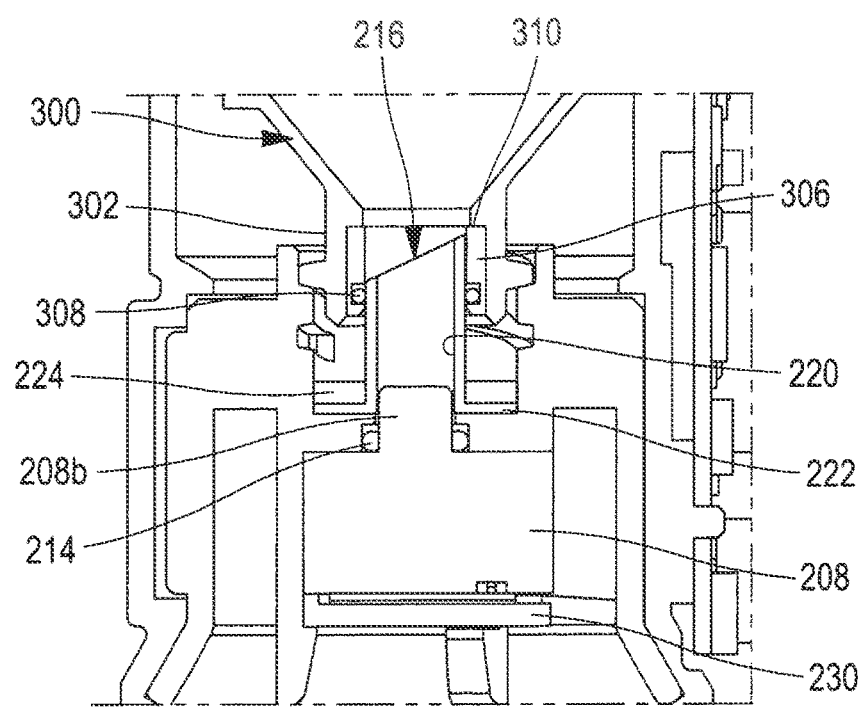
FIG. 16 is an enlarged view of details which represents the insertion of the storage container in the apparatus before opening of a valve of the storage container by the needle of the dispensing unit.

With reference to FIG. 16, the device for dispersing of the substance contained in the storage container 300 comprises the porous body 208 previously described, the base of which cooperates with the heating unit, the electrical circuit 230 of which is represented. The lug 208b of the porous body is surmounted by a hollow needle 220, with the lug 208b fitting into the base 222 of the needle. The base 222 extends radially until it covers the upper surface of the porous body. In order to ensure a sealed connection between the lug and the needle, an O-ring seal 214, surrounding the lug completely, is placed between the lug and the needle. The upper part 216 of the needle is in the form of a bevel in order to pierce more easily the stopper of the storage container as described in FIG. 12 and FIG. 14. The storage container 300 is introduced into the device via its lower part 302. The storage container is retained in the device by screwing.

When the screwing of the lower part 302 of the container begins, the needle penetrates into the ring 306, then comes into contact laterally with the O-ring seal 308 supported by the ring, such that the connection between the needle and the stopper is sealed. Then, as the screwing continues, the needle approaches the membrane 310 which is glued onto the ring.

Figure 17:
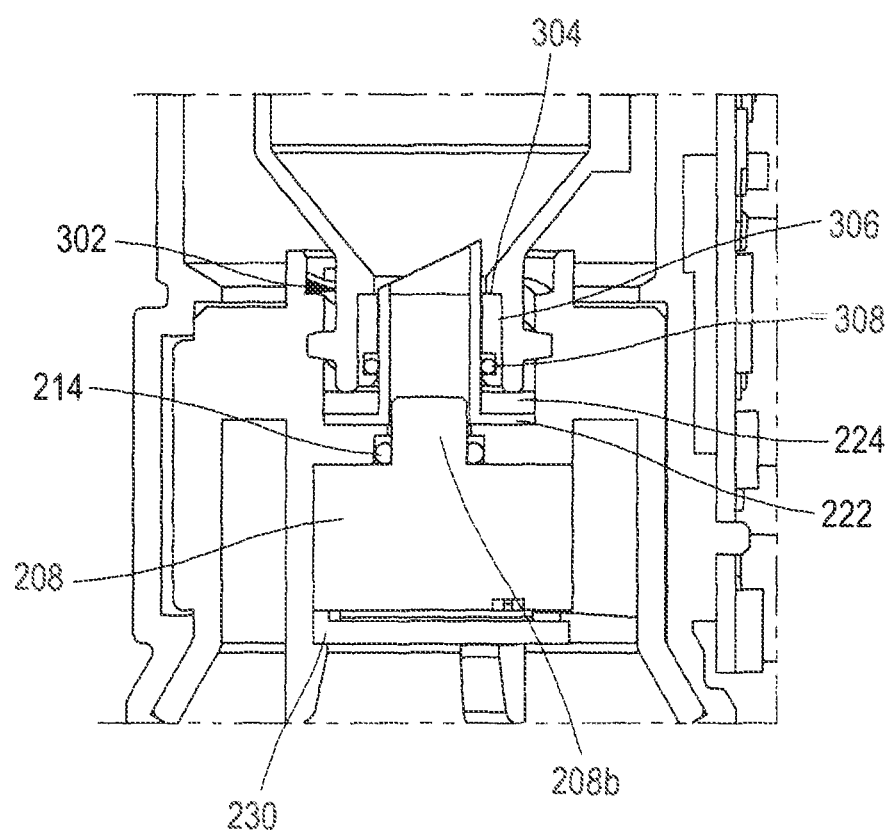
FIG. 17 is a view similar to FIG. 16 which represents the insertion of the storage container after opening of the valve.

At the end of the screwing, the bevel of the needle displaces the membrane 310 reversibly in the manner of a shutter, as illustrated in FIG. 17. The lower part 302 of the container comes into contact with a seal 224 placed on the radial extension of the base 222 of the needle. The substance can then flow into the interior of the needle. The needle guides the substance as far as the lug. The substance can then go into the micro-ducts of the porous body 208 in order to reach the evaporation surface.

If it is necessary to change the storage container, for example because it is empty or because the substance needs to be changed, the container is unscrewed. When the needle is no longer passing through the membrane, the membrane closes, thus preventing the substance from flowing.

According to a variant of the storage container 300, the alveolar retention unit described above is used in the place of the membrane 310. In this case, the dispensing unit does not comprise a needle, but a porous body which comes into contact directly with the alveolar retention unit in order to exert the capillary traction as described above.

Quantitative Example

According to an agricultural application, a solution of Codlémone is diffused in a medium, the ambient temperature of which varies typically between 0° C. and 50° C., and preferably between 10° C. and 45° C.

The apparatus is configured such that:
  with activation of the heating and/or with activation of the heating at the set temperature selected, for example between 50° C. and 65° C., the flow of evaporated solution is equal to a predefined nominal flow D, for example between 1 mg/h and 100 mg/h, preferably between 5 mg/h and 20 mg/h;
  without activation of the heating, i.e. at ambient temperature, the evaporated flow is lower than D/10, and preferably lower than D/50.

Relevant parameters for regulation of the nominal flow D are not only the operating temperature and the viscosity of the solution, but also structural parameters, such as the dimensions of the dispensing unit, in particular the area of its evaporation surface.

Some of the elements described, in particular the control device, the control boards or the electronic controllers, can be produced in different forms, in a unitary or distributed manner, by means of hardware and/or software components. Hardware components which can be used are specific ASIC integrated circuits, FPGA programmable logic networks or microprocessors. A local clock and/or a network clock can be incorporated in these elements in order to provide temporal references.

Although the invention has been described in association with a plurality of particular embodiments, it will be appreciated that it is in no way limited to these, and that it comprises all the techniques which are the equivalents of the means described, as well as their combinations, provided that these come within the scope of the invention.

The use of the verbs "contain", "comprise" or "include" and their conjugated forms does not exclude the presence of other elements, or steps other than those indicated in the claim.

In the claims, any reference sign in brackets can not be interpreted as a limitation of the claim.

The invention claimed is:

1. An apparatus for dispersing in the air, in the vapor state, a substance which is in the liquid state at ambient temperature, and is contained in at least one storage container, the apparatus comprising:
   a ventilation system comprising a duct which opens out into the open air, and is configured to permit the passage of a flow of air into the duct;
   a at least one dispensing unit which is designed to be supplied with the liquid substance by the at least one storage container, the at least one dispensing unit comprising micro-ducts forming an outlet which is provided in the duct in order to constitute an area of evaporation of the substance therein;
   wherein the at least one storage container contains the substance and is connected to the at least one dispensing unit, wherein the at least one storage container has a discharge orifice which is connected to the at least one dispensing unit, and is oriented downwards when the apparatus is in a position of use, the at least one dispensing unit being below the discharge orifice in the position of use,
   a heating unit which is provided on or in the at least one dispensing unit, such as to control a flow of the substance through the at least one dispensing unit, wherein the substance has a viscosity which is variable according to the temperature, said viscosity being such that the substance can not flow through the micro-ducts of the at least one dispensing unit at an ambient temperature lower than a first temperature, and wherein the heating unit is configured to heat the at least one dispensing unit to a second temperature higher than the first temperature, such that a flow of the substance through the micro-ducts of the at least one dispensing unit takes place by capillarity in the position of use.

2. The apparatus as claimed in claim 1, wherein the at least one dispensing unit comprises a porous body comprising pores, said pores constituting at least part of the micro-ducts of the at least one dispensing unit.

3. The apparatus as claimed in claim 2, wherein the pores have a diameter contained between 0.01 and 10 μm.

4. The apparatus as claimed in claim 2, wherein the porous is in the form of a cylinder.

5. The apparatus as claimed in claim 4, wherein the supply of substance is received in a blind recess provided parallel to the axis of the porous body.

6. The apparatus as claimed in claim 4, wherein the porous body comprises a lug which is provided on an upper part of said body, extends along a longitudinal axis of the porous body, and is configured to receive the substance.

7. The apparatus as claimed in claim 2, wherein the at least one dispensing unit comprises a peripheral membrane which is provided around the porous body, and is pierced with holes constituting micro-ducts.

8. The apparatus as claimed in claim 2, wherein the porous body has porosity in an inner part of the porous body which is lower than porosity in an outer part of the porous body surrounding the inner part.

9. The apparatus as claimed in claim 2, wherein the porous body comprises a wick which is made of wood, textile, ceramic or polymer.

10. The apparatus as claimed in claim 2, wherein the heating unit is placed directly on a surface of the porous body.

11. The apparatus as claimed in claim 2, wherein the porous body has at least one recess which accommodates at least part of the heating unit.

12. The apparatus as claimed in claim 1, wherein the at least one dispensing unit comprises a hollow needle which is configured to pierce a cap and/or to displace a membrane which acts as a shutter of the at least one storage container, and bring the substance contained in the at least one storage container to the area of evaporation.

13. The apparatus as claimed in claim 12, wherein the at least one dispensing unit comprises a porous body comprising pores, said pores constituting at least part of the micro-ducts of the at least one dispensing unit, and wherein the needle is disposed at one of the ends of the porous body.

14. The apparatus as claimed in claim 1, wherein the micro-ducts have a cross-section contained between $10^{-4}$ μm$^2$ and $10^6$ μm$^2$.

15. The apparatus as claimed in claim 14, wherein the micro-ducts have a cross-section contained between 0.1 μm$^2$ and $10^3$ μm$^2$.

16. The apparatus as claimed in claim 1, additionally, comprising a securing unit, the direction and/or inclination of which can be oriented relative to the duct of the ventilation system, in order to orient the duct relative to the ground when the securing unit is secured on a support.

17. The apparatus as claimed in claim 1, wherein the ventilation system comprises at least one fan which is placed in part of the duct.

18. The apparatus as claimed in claim 17, wherein said apparatus comprises a regulator unit for a flow of air in the duct, which unit is configured to control the at least one fan in order to regulate a flow of air in the duct.

19. The apparatus as claimed in claim 1, wherein the ventilation system comprises openings provided in an end wall of the duct, and adjustable shutters which equip said openings, in order to make it possible to regulate a cross-section of passage of the openings.

20. The apparatus as claimed in claim 19, wherein said apparatus comprises a regulator unit for a flow of air in the duct, which unit is configured to control the fan and/or the adjustable shutters in order to regulate a flow of air in the duct.

21. The apparatus as claimed in claim 1, additionally comprising a control device which is configured to control the heating unit according to a set temperature in the at least one dispensing unit.

22. The apparatus as claimed in claim 21, wherein the heating unit comprises at least one electronic board and at least one electrical resistor which is supplied electrically by the electronic board.

23. The apparatus as claimed in claim 22, wherein the control device is provided on the electronic board.

24. The apparatus as claimed in claim 21, wherein the at least one dispensing unit is equipped with a temperature sensor.

25. The apparatus as claimed in claim 24, wherein the temperature sensor is at a free end of the at least one dispensing unit.

26. The apparatus as claimed in claim 21, wherein the set temperature is defined according to the substance.

27. The apparatus as claimed in claim 26, wherein the control device is connected to a detector which is configured to detect marking at the at least one storage container indicating the substance contained in the at least one storage container, and wherein according to said marking the control device determines at least one operating parameter of the apparatus from out of the set temperature, a flow of air, and temporal indications defining a stop/operating cycle.

28. The apparatus as claimed in claim 21, wherein the control device comprises a memory which stores a table of values associating substances with set temperatures.

29. The apparatus as claimed in claim 28, additionally comprising a communication module, in order to ensure wired or non-wired communication with a data server, in order to modify the table of values.

30. The apparatus as claimed in claim 1, wherein the substance at the second temperature spreads in the liquid state on a surface of the at least one dispensing unit, which surface is situated in the ventilation system.

31. The apparatus as claimed in claim 1, wherein the heating unit is configured to regulate a flow of the substance through the at least one dispensing unit by modifying a viscosity of the substance without vaporizing the substance.

32. The apparatus as claimed in claim 1, wherein the second temperature is selected such that the flow of the substance takes place at a flow rate which is sufficiently low to prevent the formation of drops becoming detached from the at least one dispensing unit, and sufficiently great for the area of evaporation to remain permanently wetted despite the flow of air sent by the ventilation system.

33. The apparatus as claimed in claim 32, wherein the at least one storage container does not have an opening other than the discharge orifice, said at least one storage container containing a gaseous phase which occupies at least 20% of the volume of the at least one storage container, as well as the liquid substance.

34. The apparatus as claimed in claim 32, wherein the at least one storage container comprises an outer tank and an inner tank which is accommodated in the outer tank, the inner tank being connected to the at least one dispensing unit via the discharge orifice, and having a vent which is connected to the atmosphere at an end opposite the discharge orifice, wherein an orifice for communication between the outer tank and the inner tank is provided in the vicinity of the discharge orifice, the outer tank not having an opening other than said orifice for communication.

35. The apparatus as claimed in claim 1, wherein the at least one storage container is fitted removably in the apparatus, and is configured such as to be able to be removed from the apparatus without loss of substance.

36. The apparatus as claimed in claim 35, wherein the at least one storage container is fitted in the apparatus by being screwed or snapped in.

37. The apparatus as claimed in claim 1, wherein the at least one dispensing unit has a first surface which faces towards the at least one storage container, and is provided with a seal ensuring a sealed connection between the at least one dispensing unit and the at least one storage container, and a second surface which is provided in the ventilation system.

38. The apparatus as claimed in claim 1, wherein the at least one storage container comprises a seal which is provided around the discharge orifice such as to ensure a sealed connection between the at least one storage container and the at least one dispensing unit.

39. The apparatus as claimed in claim 1, wherein the at least one storage container comprises an alveolar retention unit which is provided in the at least one storage container in a manner adjacent to the discharge orifice, in order to limit a flow of the substance.

40. The apparatus as claimed in claim 1, wherein the substance has a boiling temperature contained between 30° C. and 400° C. at atmospheric pressure.

41. The apparatus as claimed in claim 1, wherein the substance has a viscosity greater than 1 cPa·s at 25° C., and less than 1 cPa·s at 60° C.

42. The apparatus as claimed in claim 1, wherein the substance is a solution comprising at least one compound taken from the group formed by odiferous agents which can be used for people or animals, semiochemical substances, cosmetic agents, essential oils, perfumes and phytosanitary and agricultural agents.

43. The apparatus as claimed in claim 42, wherein the odiferous agents which can be used for animals are selected from amongst fatty acids or the esterified form of said fatty acids.

44. The apparatus as claimed in claim 43, wherein the fatty acid or the esterified form of said fatty acid is methyl oleate, methyl palmitate, dimethyl azelate, or dimethyl pimelate.

45. The apparatus as claimed in claim 42, wherein the substance is a solution which contains at least one semiochemical substance, said semiochemical substance being at least one pheromone, an allomone or a kairomone of natural or synthetic origin.

46. The apparatus as claimed in claim 42, wherein the substance is a solution which contains at least one semiochemical substance, said at least one semiochemical substance being at least one pheromone which is or is not sexual, an allomone, a synomone or a kairomone, designed to provoke a positive or negative response relative to a species concerned of arthropod.

47. The apparatus as claimed in claim 46, wherein the positive or negative response relative to the species concerned of arthropod is a behavioral result which is confusion, attraction, or repulsion.

48. The apparatus as claimed in claim 47, wherein said confusion is sexual confusion.

49. The apparatus as claimed in claim 47, wherein said attraction is sexual attraction.

50. The apparatus as claimed in claim 46, wherein the arthropod is an arachnid or a hexapod.

51. The apparatus as claimed in claim 46, wherein the arthropod is an insect.

52. The apparatus as claimed in claim 51, wherein the insect is a harmful insect.

53. The apparatus as claimed in claim 42, wherein the substance is a solution containing at least one semiochemical substance, the at least one semiochemical substance being at least one pheromone or a sexual pheromone, an allomone, a synomone or a kairomone designed to provoke a positive or negative response relative to a species concerned in the classes mammalia and ayes.

54. The apparatus as claimed in claim 53, wherein the positive or negative response relative to the species concerned in the classes mammalia and ayes is a behavioral result which is pacification, relaxation, mood elevation, or intimidation.

55. The apparatus as claimed in claim 1, wherein the substance comprises a solvent selected from amongst isopropyl myristate, dipropylene glycol, monomethyl dipropylene glycol ether, and an isoparaffinic hydrocarbon.

56. The apparatus as claimed in claim 1, comprising a plurality of the at least one storage containers each containing a substance in liquid form, or a plurality of substances in liquid form which are miscible with one another.

57. The apparatus as claimed in claim 56, wherein all or part of the plurality of at least one storage containers is supported on the exterior by the duct (2) of the ventilation system.

58. The apparatus as claimed in claim 56, comprising a plurality of the at least one dispensing units each dispensing unit comprising a porous body comprising pores said pores constituting at least part of the micro-ducts of that dispensing unit, wherein each of the at least one storage containers is associated with a porous body of an associated dispensing unit, the porous bodies being placed in the interior of the duct of the ventilation system, and being disposed with offsettings of the porous bodies in a longitudinal direction of the duct.

59. The apparatus as claimed in claim 1, wherein the first temperature is equal to 30° C.

60. The apparatus as claimed in claim 1, wherein the first temperature is equal to 50° C. and the substance is a solution of Codlémone.

\* \* \* \* \*